(12) United States Patent
Kinne et al.

(10) Patent No.: US 6,512,355 B1
(45) Date of Patent: Jan. 28, 2003

(54) DEVICE AND METHOD FOR INSPECTION AND DETECTION OF A MATERIAL BY OBSERVING A HIGH-VOLTAGE WAVEFORM PRODUCED BY THAT MATERIAL

(75) Inventors: William E. Kinne, Edgewood, MD (US); Albert P. Ross, North East, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/400,146

(22) Filed: Sep. 21, 1999

(51) Int. Cl.$^7$ .................. G01N 27/00; G01N 27/62; G01R 23/16; G01R 29/12
(52) U.S. Cl. ............... 324/71.1; 324/76.12; 324/457; 324/464
(58) Field of Search ................ 324/71.1, 558, 324/557, 464, 500, 379, 457, 76.12, 76.22, 536

(56) References Cited

U.S. PATENT DOCUMENTS

| 4,125,805 A | * | 11/1978 | Nagamatsu | 324/54 |
| 4,338,568 A | * | 7/1982 | Yang | 324/466 |
| 4,980,645 A | * | 12/1990 | Soma et al. | 324/541 |
| 5,155,437 A | * | 10/1992 | Frus | 324/380 |
| 5,198,773 A | * | 3/1993 | Latta | 324/464 |
| 6,078,180 A | * | 6/2000 | Jenkinson | 324/536 |

* cited by examiner

Primary Examiner—N. Le
Assistant Examiner—Anjan K. Deb
(74) Attorney, Agent, or Firm—Ulysses John Biffoni; Vincent J. Ranucci (57) ABSTRACT

Materials display innate resistance, capacitance, and inductance (RCL) properties and can therefore be distinguished in accordance with these properties. A high voltage is applied across a material, and a waveform is obtained whose rise time, frequency content, duration, and fall time represent the RCL properties of the material. The high voltage can be applied by passing air containing the material through a pair of screens held at a potential difference or by gluing a sample of the material to two rods held at a potential difference. The voltage may or may not be enough to cause the material to arc.

21 Claims, 8 Drawing Sheets

DEVICE AND METHOD FOR INSPECTION AND DETECTION OF A MATERIAL BY OBSERVING A HIGH-VOLTAGE WAVEFORM PRODUCED BY THAT MATERIAL

GOVERNMENT INTEREST

The invention described herein may be manufactured, used and licensed by or for the U.S. Government.

FIELD OF THE INVENTION

The present invention is directed to a device and method for inspection and detection of a fiber material by applying a high voltage to the material and observing its high-voltage waveform.

DESCRIPTION OF RELATED ART

There is a need in the art to detect low impedance fiber in extremely low concentrations. Current detectors, such as the ETI high-voltage plate, detect only the presence of low impedance fibers and provide no further differentiation or other information.

SUMMARY OF THE INVENTION

It is an object of the invention to provide a device and method for discerning material type or measuring differences in material quality caused by differences in crystalline structure.

It is another object of the invention to provide such a device and method for detection and quality control.

To achieve these and other objects, the present invention is directed to a device for taking data representative of a material for analysis of the material, the device comprising: a voltage supply for supplying a voltage; testing means for receiving the material and for applying the voltage across the material to obtain a resulting waveform; and detecting means for detecting the resulting waveform to produce an output representing the resulting waveform.

The present invention is further directed to a method of taking data representative of a material for analysis of the material, the method comprising: (a) applying the voltage across the material to obtain a resulting waveform; and (b) detecting the resulting waveform to produce an output representing the resulting waveform.

The invention employs the principle that all solids, at least in theory, display innate resistance, capacitance, and inductance (RCL) properties. More specifically, all material can be analyzed in terms of an equivalent circuit having resistive, capacitive, and inductive elements. A crystalline material should have such elements in series. The equivalent circuits, and thus the materials themselves, display responses having distinctive patterns when energized with high voltage.

Thus, when a material is activated with sufficient voltage, distinct wave forms should appear. The differential patterns should be discernible by rise time, frequency content, duration, and fall time.

The invention allows detection of fiber in extremely low concentrations. It also allows detection and differentiation of any material of sufficient conductivity to initiate an arc.

The invention allows inspection analysis of known materials for density and crystalline structure and also allows detection of material types in an unknown environment. Minor differences in crystalline structure within material types will affect the equivalent circuits and will thus be measurable. Hardness, crystalline structure, and thickness can be discerned.

The invention can be used in a production environment to monitor material quality.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENTS

Figure 1:
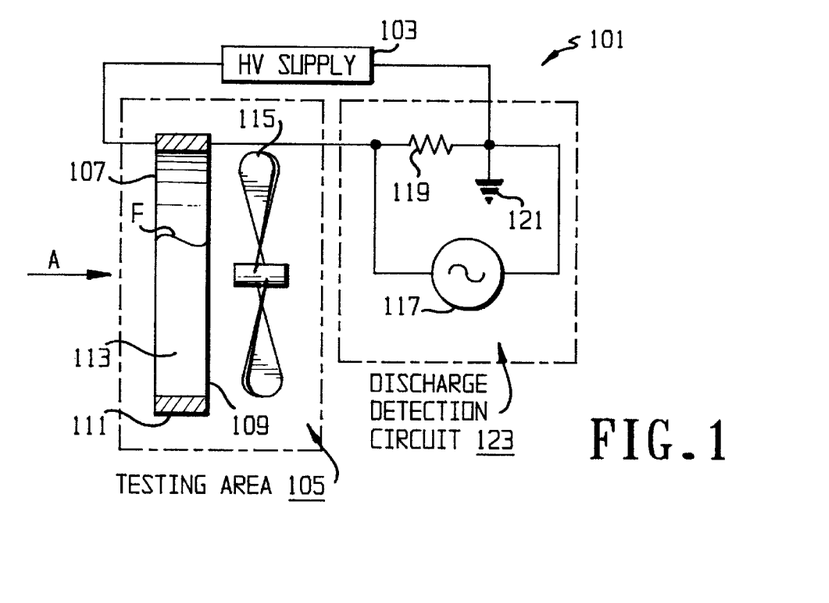
FIG. 1 shows a block diagram of one setup according to the preferred embodiment.
Figure 2:
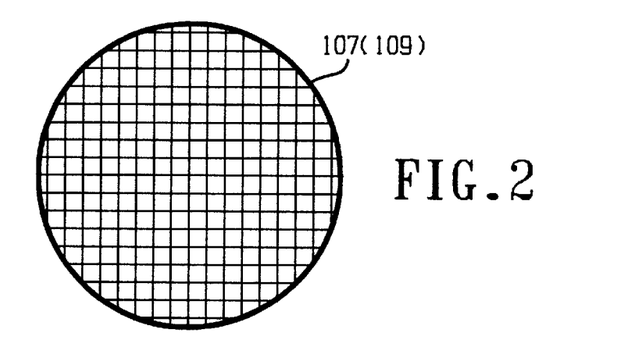
FIG. 2 shows one of the screens used in the setup of FIG. 1.

FIG. 1 shows one setup according to a preferred embodiment of the present invention. As shown in FIG. 1, setup 101 includes high-voltage (HV) supply 103, which can be a high-voltage capacitor, to supply high voltage to the material to be tested. Testing area 105 includes two screens 107, 109 of brass or the like, which are mounted in parallel on air-flow tube 111 of an insulating material such as that sold under the trade name PLEXIGLAS so as to have a separation of ⅛ to 1 inch, typically ⅜ inch. This separation defines cavity 113 between screens 107 and 109. Each of screens 107 and 109 has the appearance shown in FIG. 2. Muffin fan or other blowing device 115 drives air or another fluid containing the material to be tested at a rate of about 7 m/sec to move in the direction indicated by arrow A. Alternatively, testing area 105 could be oriented so that the material to be tested could fall through screens 107 and 109. Oscilloscope 117, resistor 119 (such as a 1 Ω or 10 Ω resistor, although any suitable value can be used), and grounding connection 121 form discharge detection circuit 123. Grounding connection 121 grounds one terminal of HV supply 103 and one terminal of oscilloscope 117 and also grounds screen 109 through resistor 119. With the connection shown in FIG. 1, oscilloscope 117 measures the voltage drop across resistor 119.

Screen 107 is connected to one terminal of HV supply 103, while screen 109 is grounded through resistor 119 of discharge detection circuit 123, so that screens 107 and 109 are at voltages of $V_a$ and $V_b$, respectively. These voltages can be selected as needed; a voltage difference $V_a-V_b$ between 1,800 and 7,000 V is generally used, while a voltage difference of 4,000 V or more is required to fire an arc if the material being tested is human hair.

Figure 3:
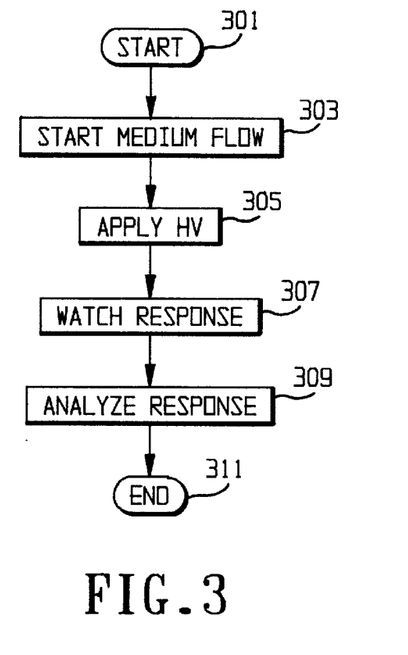
FIG. 3 shows a flow chart of operational steps in carrying out the preferred embodiment.

The operation of setup 1 will now be explained with reference to the block diagram of FIG. 1 and the flow chart of FIG. 3. The operation starts in step 301. In step 303, the medium flow is started, e.g., by turning on fan 115, so that the fluid containing the medium to be tested flows through testing area 105. In this way, at least some of the fibers, such as fiber F shown in FIG. 1, can contact both screens 107 and 109 simultaneously. In step 305, the high voltage is applied from HV supply 103 to screens 107 and 109, e.g., by discharging a capacitor. Thus, the HV is applied instantaneously across the ends of fiber F, so as possibly to cause the fiber to arc; the voltage needed to cause the arc depends on the material. Although FIG. 3 shows step 303 to precede step 305, the order of step 303 and step 305 may be reversed. In step 307, the response is watched on oscilloscope 117, which can have capabilities such as printing the response or storing it on disk. In step 309, the response is analyzed, e.g., by comparing it with archived or calculated responses. The frequency content and duration of a discharge from the material manifested in the response are dependent on the material. The initial effects are believed to be skin effects as the electrons rush across the surface of fiber F from one screen to the other. Suitable software can be written for the analysis. In step 311, the operation ends.

Tests verified that the resultant waveforms were different for the various materials tested, i.e., graphite, coated graphite, human hair, stainless steel, and spider silk. All displayed significant differences in waveform characteristics. Since these materials are non-polar in nature, no polarization effect was either expected or observed. The voltages used in step 305 ranged from 1,800 V to 7,000 V; the coated graphite and the human hair did not arc at less than 4,000 V.

Figure 4:
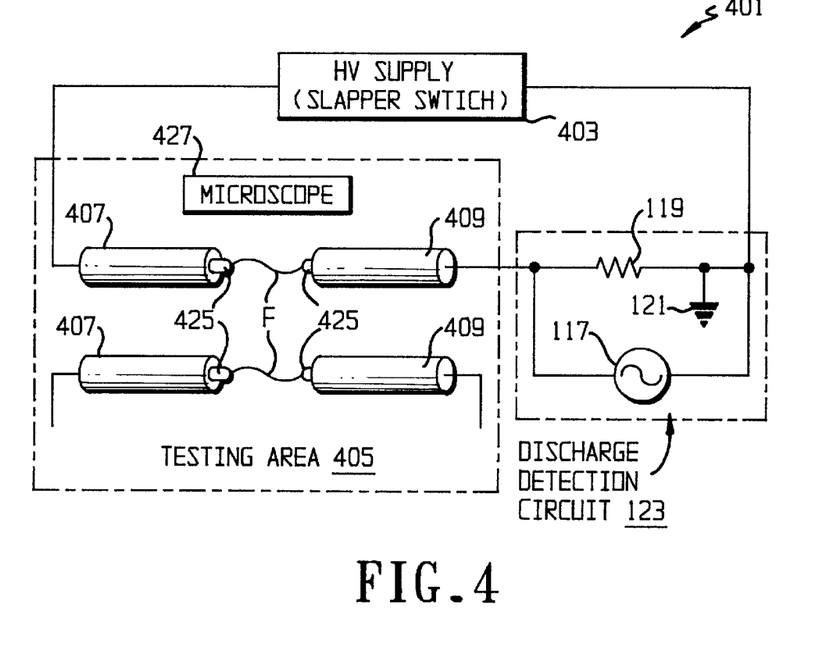
FIG. 4 shows a modified version of the setup of FIG. 1.

There is the concern that in setup 101 of FIG. 1, the resultant waveform is heavily influenced by the RCL of setup 101 itself. Moreover, the orientation of the fiber may give false results. To overcome these concerns and generally to provide a cleaner, more efficient and more tractable way to gather data, a modified setup was developed, which will now be explained with reference to FIG. 4. In FIG. 4, elements which are the same as those in FIG. 1 are represented by the same element numbers, while elements which are modified from those in FIG. 1 are represented by element numbers increased by 300.

FIG. 4 shows modified setup 401, which uses discharge detection circuit 123 in combination with a more robust HV supply 403 and testing area 405 improved for individual mounting of fibers. HV supply 403 uses a slapper switch and will be described in detail below. Testing area 405 uses brass rods 407, 409, or other suitable mounting elements formed out of any suitable material, to which fiber F is secured with silver paint 425, which has a drying time of approximately two hours. Any other suitable manner of securing fiber F to rods 407, 409 can be used. Multiple pairs of brass rods 407, 409 can be provided to form multiple testing jigs within testing area 405 so that multiple fibers can be mounted at a time; setups such as setup 401 have been built with up to five such pairs of rods. More than the two pairs of brass rods 407, 409 shown in FIG. 4 may be employed. Microscope 427, such as a binocular microscope, can be used to mount and inspect the fibers.

HV supply 403 is of the "slapper switch" type and provides a high-voltage pulse from a predetermined capacitance and switch-on time. HV supply 403 is designed for testing and evaluation of bridgewire detonators.

Figure 5:
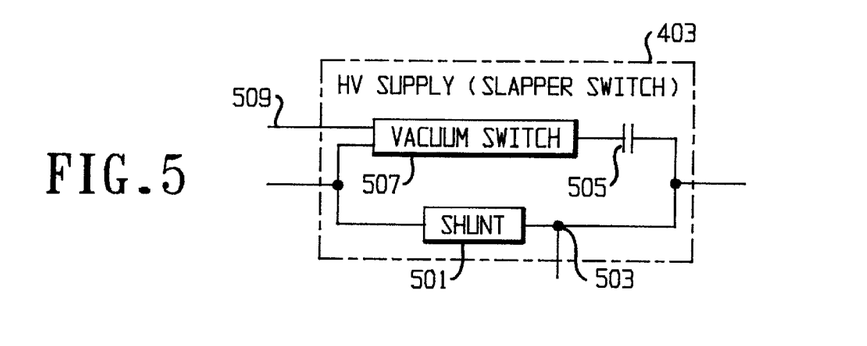
FIG. 5 shows a block diagram of the high-voltage supply used in the setup of FIG. 4.

As shown in FIG. 5, HV supply 403 includes the following components. Low-impedance shunt 501 allows analysis of the voltage supplied and includes monitoring point 503 to allow monitoring of the HV supply by any suitable monitoring equipment. The voltage is stored in high-capacitance capacitor 505, whose capacitance is selected to provide the desired voltage to setup 401. Capacitor 505 is discharged by a fast-acting switch such as vacuum switch 507 under control of a low-voltage firing input received through input lead 509.

Figure 6:
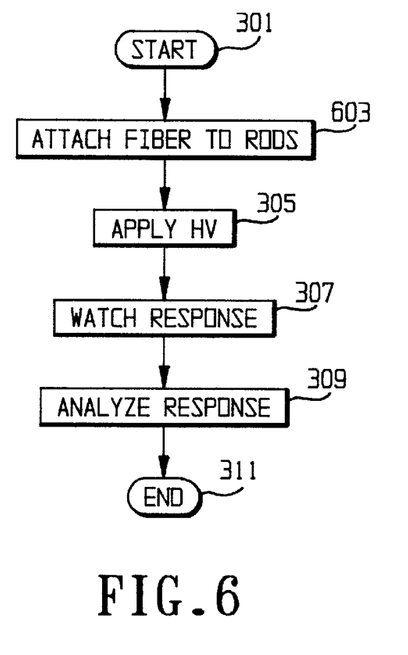
FIG. 6 shows a flow chart of the operational steps of FIG. 3 modified for the setup of FIG. 4.

FIG. 6 shows a series of operational steps for using setup 401. This series of operational steps is the same as in FIG. 3, except that step 303 is replaced with step 603 of attaching fiber F to rods 407 and 409.

EXAMPLES

Experimental results from setup 401 will now be described with reference to FIGS. 7–12. In these figures, the x axis represents time in seconds, while the y axis represents voltage in kV.

Figure 7:
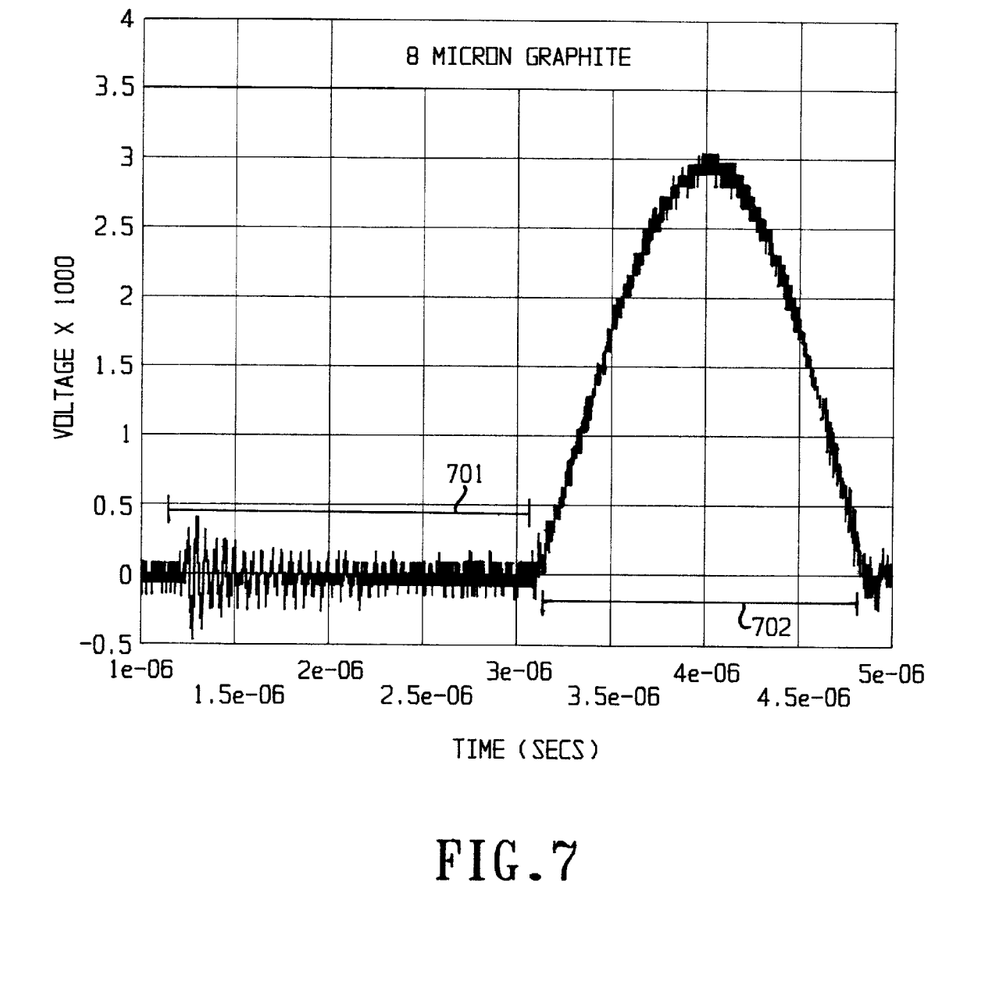
FIGS. 7–12 show experimental results.

FIG. 7 shows experimental results obtained with 8-micron graphite. The curve has regions 701 and 702. Region 701 corresponds to the application of ~2,000 V to provide a "ramp-up" in voltage. This region contains the spectral information characteristic of the material. Region 702 shows a voltage arc associated with vaporization of the material.

The remaining results show corresponding regions, except that when arcing does not occur, neither does the region corresponding to region 702.

Figure 8:
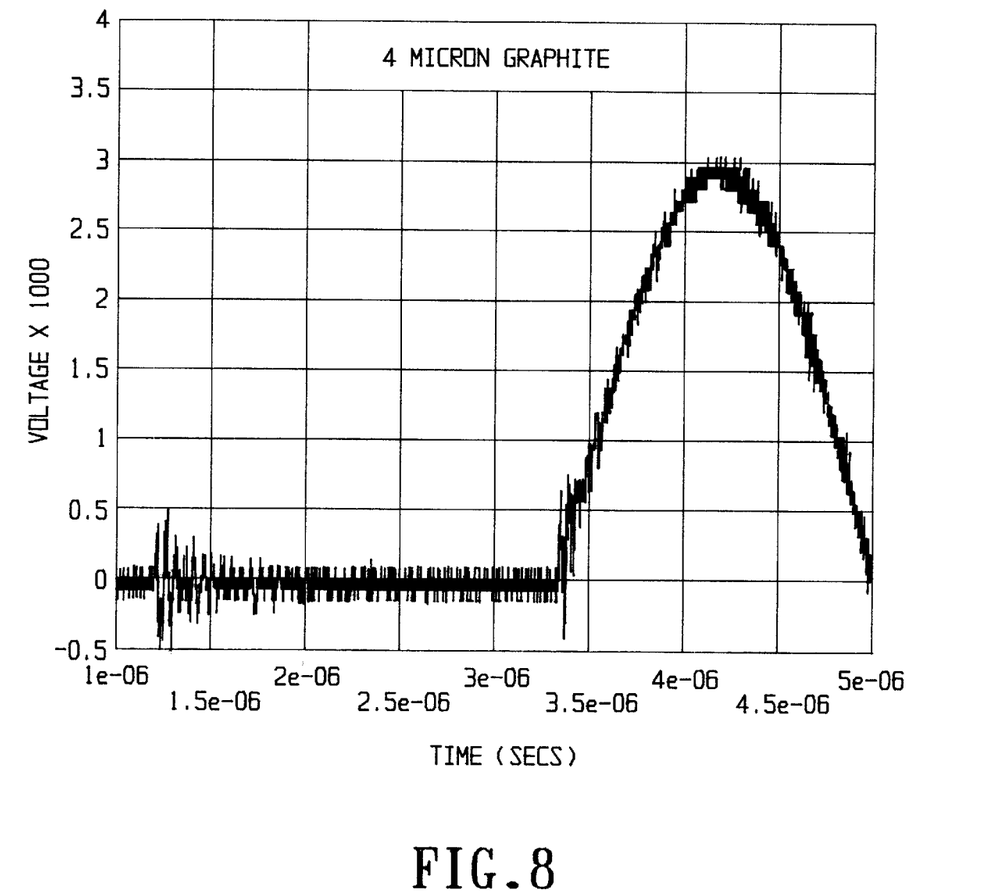
Figure 9:
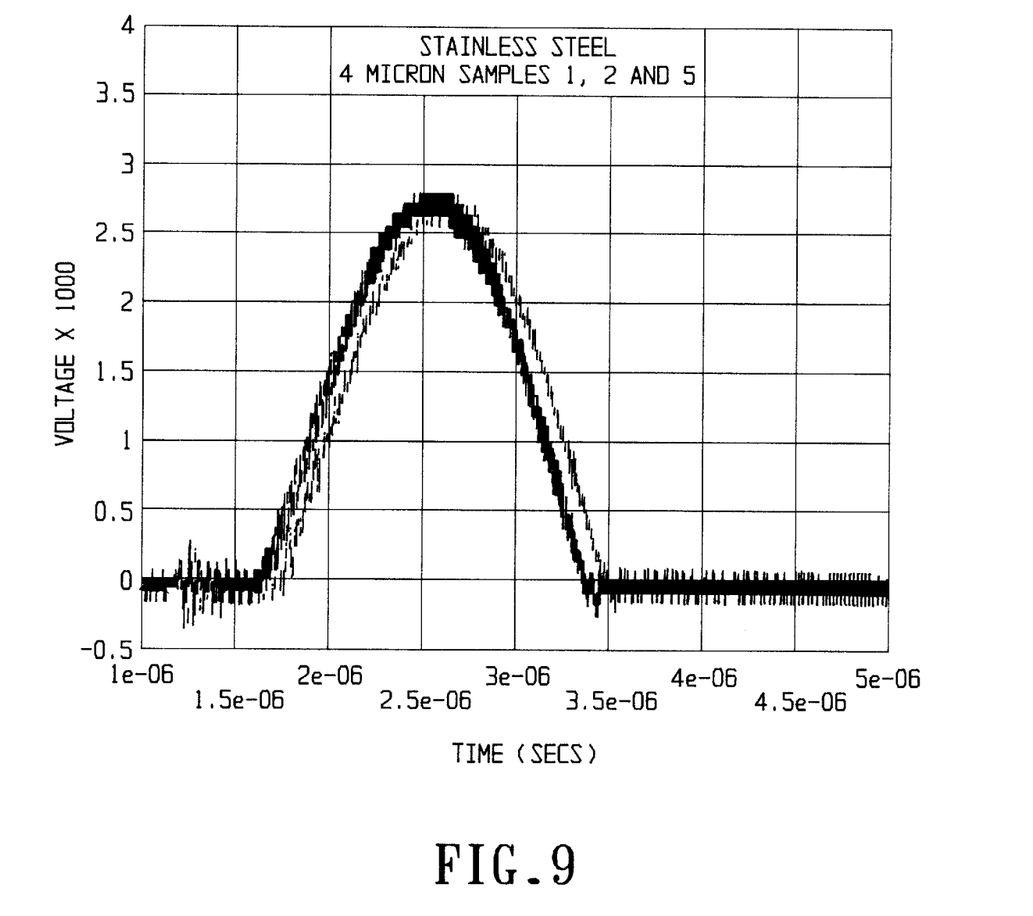
Figure 10:
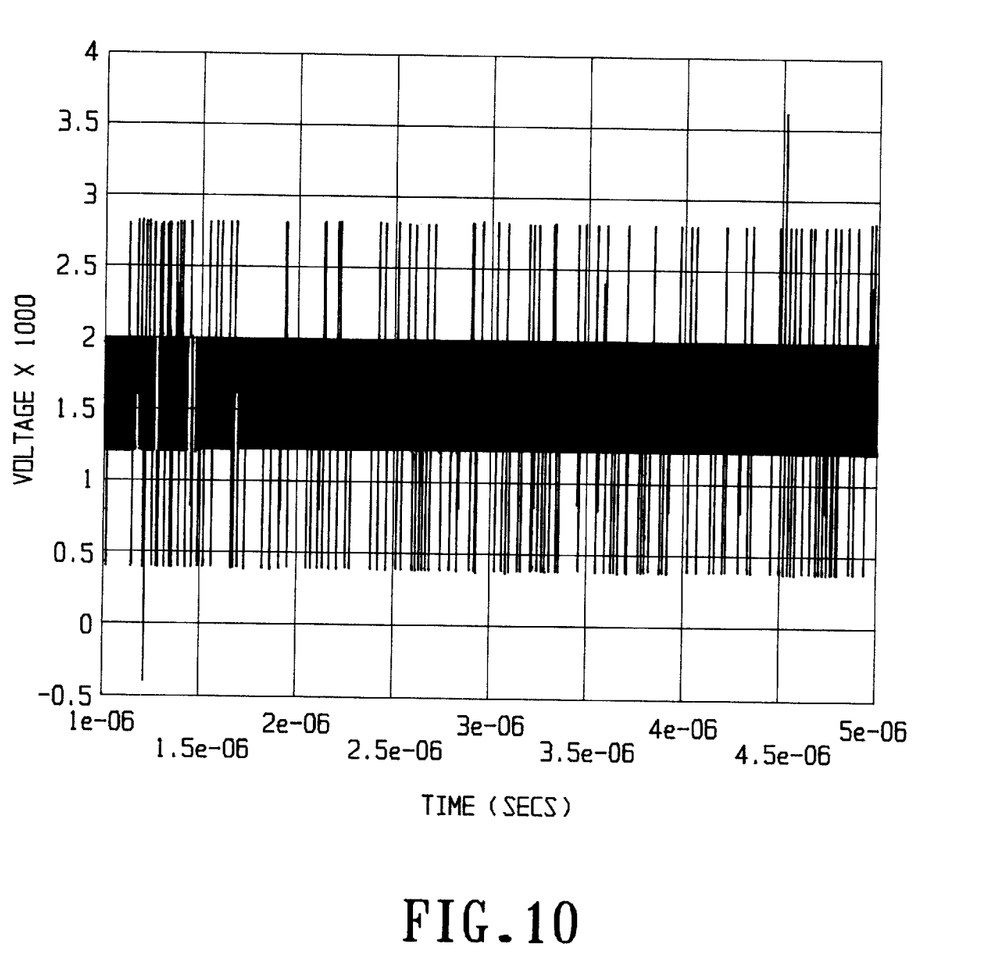
Figure 11:
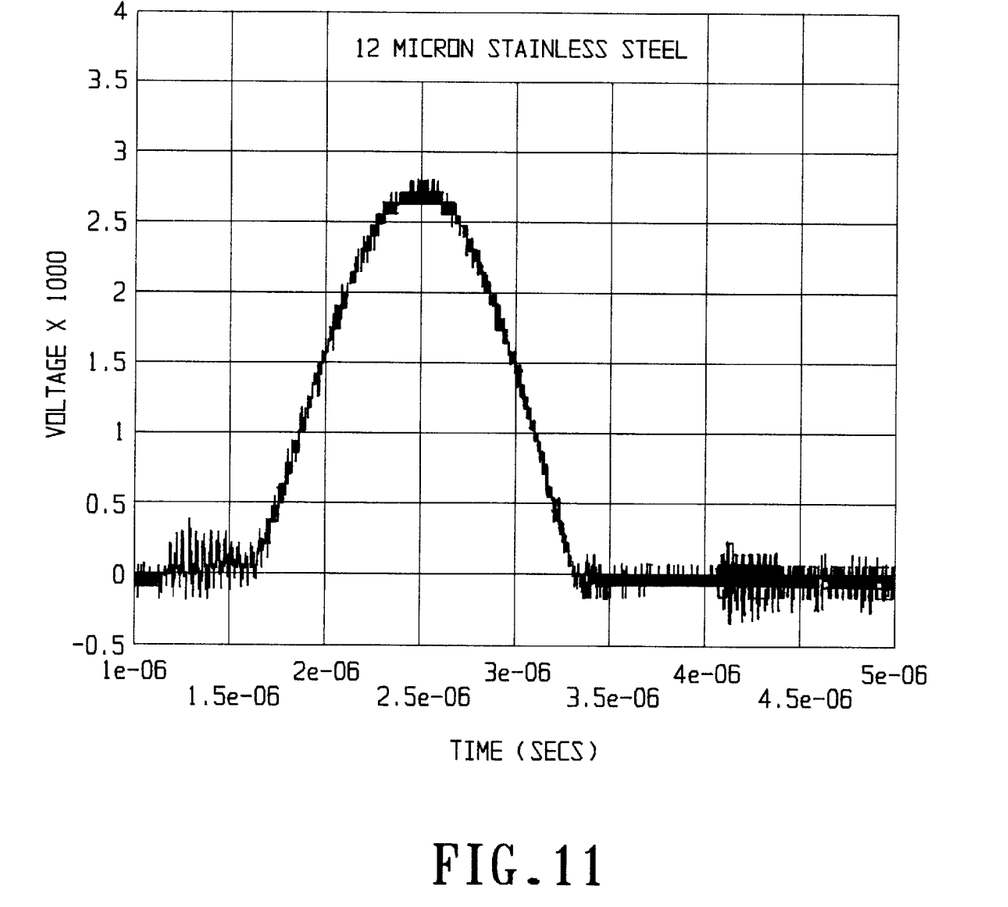
Figure 12:
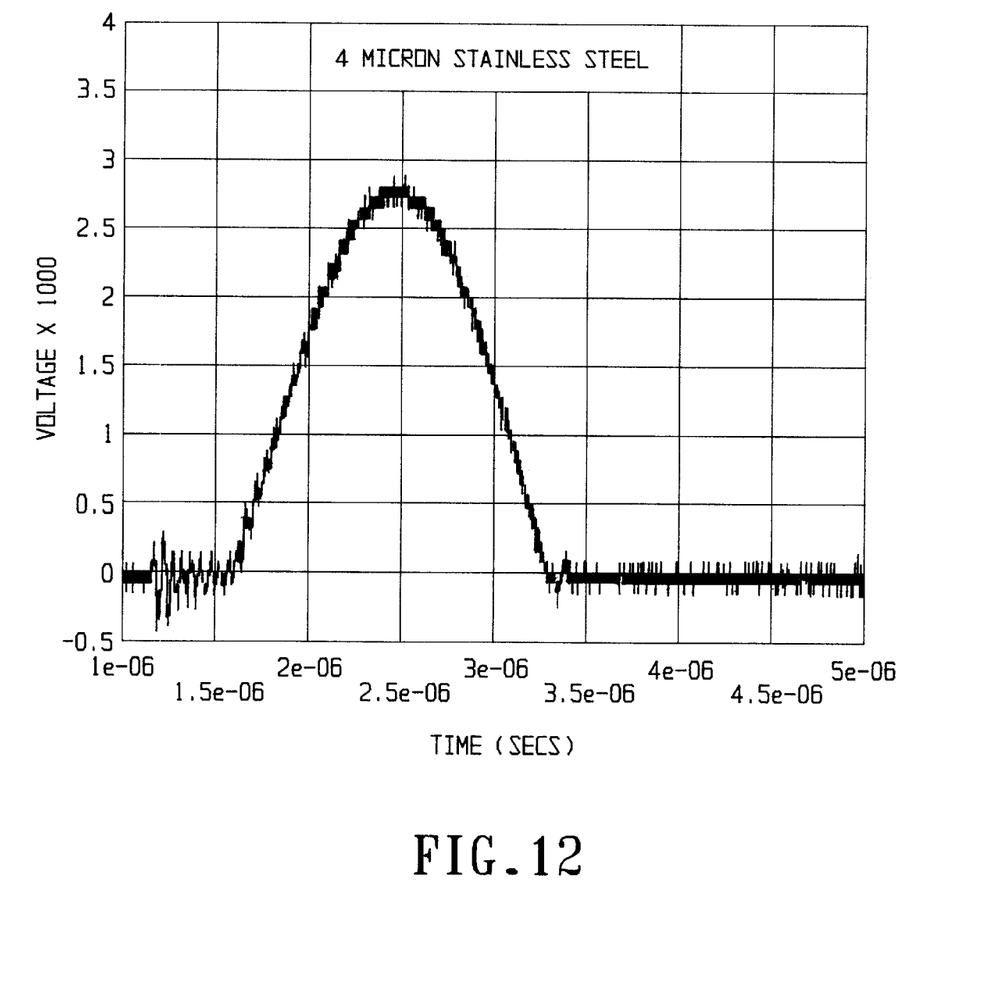

FIG. 8 shows results for 4-micron graphite. FIG. 9 shows curves for three samples of 4-micron stainless steel when placed in three respective different positions 1, 2 and 5, i.e., between different brass rods 407, 409 of the device setup 401 having five pairs of rods 407, 409 in the setup. Positions 3 and 4 are not shown because the samples fractured in handling. FIG. 10 shows results for human hair, which acts as a high-impedance circuit. Arcing did not occur in this sample. FIG. 11 shows results for 12-micron stainless steel, while FIG. 12 shows results for 4-micron stainless steel.

While two variations of a preferred embodiment of the invention have been described in detail, those skilled in the art who have reviewed this disclosure will readily appreciate that other embodiments can be described within the scope of the invention. For example, modifications disclosed together can be used separately, while modifications disclosed separately can be combined. Also, any conventional analytical hardware, software, or techniques can be incorporated into setups according to the invention. Any disclosed process can be automated. The data collected can be combined with electron microscope pictures, manufacturing information, low-voltage measurements, or any other information useful in analysis of the material.

We claim:

1. A device for taking data representative of a test material for analysis of the test material, said device comprising:
   (a) a voltage supply;
   (b) testing means for receiving said test material and for applying a voltage from said voltage supply across said material to obtain a resulting waveform specific to said material;
   (c) detecting means for detecting said resulting waveform and producing an output representing said resulting waveform for said test material; and
   (d) an archive of outputs representing waveforms for known materials, so that the output waveform of said test material obtained in step (c) can be compared with said archived outputs for known materials in order to analyze, inspect, or identify said test material.

2. A device as in claim 1, wherein the voltage supply comprises a capacitor.

3. A device as in claim 1, wherein the voltage supply comprises a slapper switch.

4. A device as in claim 1, wherein the testing means comprises a pair of screens for applying the voltage across the material as the material passes through the pair of screens.

5. A device as in claim 4, wherein the testing means further comprises a fan for causing a fluid containing the material to pass through the pair of screens.

6. A device as in claim 1, wherein the testing means comprises a pair of mounting elements to which the material is mounted.

7. A device as in claim 6, wherein each of the pair of mounting elements is a rod.

8. A device as in claim 6, further comprising an adhesive for adhering the material to the pair of mounting elements.

9. A device as in claim 8, wherein the adhesive comprises silver paint.

10. A device as in claim 1, wherein the detecting means comprises an oscilloscope.

11. A device as in claim 10, wherein the detecting means further comprises a resistor connected between the testing means and ground, the oscilloscope and the resistor being connected such that the oscilloscope measures a potential drop across the resistor.

12. A device as in claim 1, wherein the voltage is sufficient to cause the material to arc.

13. A device as in claim 1, wherein the voltage is not sufficient to cause the material to arc.

14. A method of taking data representative of a test material for analysis, inspection, or identification of the test material, said method comprising the steps of:

(a) applying a voltage across said test material to obtain a resulting waveform specific for said material;

(b) detecting a resulting waveform and producing an output representing the resulting waveform for said test material; and (c) comparing said output representing said resulting waveform for said test material with archived outputs representing resulting waveforms for known material in order to analyze, inspect, or identify said test material.

15. A method as in claim 14, wherein step (a) comprises (i) applying the voltage to a pair of screens and (ii) applying the voltage across the material as the material passes through the pair of screens.

16. A method as in claim 14, wherein step (a) comprises mounting the material to a pair of mounting elements.

17. A method as in claim 16, wherein each of the pair of mounting elements is a rod.

18. A method as in claim 16, wherein the step of mounting comprises adhering the material to the pair of mounting elements.

19. A method as in claim 18, wherein the adhesive comprises silver paint.

20. A method as in claim 14, wherein the voltage is sufficient to cause the material to arc.

21. A method as in claim 14, wherein the voltage is not sufficient to cause the material to arc.

* * * * *